US00PP33872P3

(12) United States Plant Patent
Carmi et al.

(10) Patent No.: US PP33,872 P3
(45) Date of Patent: Jan. 18, 2022

(54) MEDITERRANEAN MANDARIN TREE NAMED 'SIGAL'

(50) Latin Name: ***Citrus deliciosa* Ten (ex *C. reticulata* Blanco)**
Varietal Denomination: SIGAL

(71) Applicant: State of Israel, Ministry of Agriculture & Rural Development, Agricultural Research Organization, Rishon Lezion (IL)

(72) Inventors: Nir Carmi, Ramat Efal (IL); Yoram Eyal, Shimshon (IL); Hanna Neuman-Leshem, Hemed (IL); Ahuva Frydman-Shani, Ramat-Gan (IL); Aliza Vardi, Ramat-Gan (IL); Avraham Elhanati, Holon (IL); Yosef Yaniv, Rehovot (IL); Kanonich Yeoshua, Yavne (IL); Fanberstein Luba, Rishon Lezion (IL)

(73) Assignee: State of Israel, Ministry of Agriculture & Rural Development, Agricultural Research Organization, Rishon Lezion (IL)

( * ) Notice: Subject to any disclaimer, the term of this patent is extended or adjusted under 35 U.S.C. 154(b) by 0 days.

(21) Appl. No.: 16/873,556

(22) Filed: May 1, 2020

(65) Prior Publication Data

US 2021/0345534 P1 Nov. 4, 2021

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./202, 201
CPC ..... A01H 5/0806
See application file for complete search history.

(56) References Cited

PUBLICATIONS

PLUTO UPOVROM Plant Variety Database 20210209 Citation as per QZ PBR 20131112; Aug. 17, 2013; 1 page.*

* cited by examiner

*Primary Examiner* — Kent L Bell
(74) *Attorney, Agent, or Firm* — Foley & Lardner LLP

(57) ABSTRACT

A new and distinct mandarin variety of *Citrus deliciosa* Ten. named 'SIGAL', particularly characterized by easy-peeling, late ripening, high quality flavor, flattened fruit shape at stalk end, medium size fruit, dark orange skin color and lacking seed.

6 Drawing Sheets

Botanical name of the genus and species of the plant claimed: *Citrus deliciosa* Ten (ex *C. reticulata* Blanco).
Variety denomination: 'SIGAL'.

BACKGROUND OF THE INVENTION

The present invention relates to a new and distinct variety of a mandarin tree, botanically known as *Citrus deliciosa* Ten., of the Rutaceae Family, and hereinafter referred to by the variety denomination 'SIGAL'.

The new *Citrus deliciosa* Ten. variety is a product of a planned breeding program conducted by the inventors, Nir Carmi, Yoram Eyal, Hanna Neuman-Leshem, Ahuva Frydman-Shani, Yosef Yaniv, Aliza Vardi, Avraham Elhanati, Kanonich Yehoshua and Fanberstein Luba in Bet Dagan, Coastal Plain, Israel. The objective of the breeding program was to develop a new late-ripening, easy-peeling, seedless mandarin variety, with high quality and excellent flavor.

The new *Citrus deliciosa* Ten. variety originated from a cross made by the inventors in 1995 in Bet Dagan, Coastal Plain, Israel. The female or seed parent is the *Citrus deliciosa* Ten. designated 'ORAH' (unpatented). The male or pollen parent is the *Citrus deliciosa* Ten. designated 'SHAM' (patented U.S. Plant Pat. No. 13,634). The new *Citrus deliciosa* Ten. 'SIGAL' was observed and selected by the inventors within the progeny of the stated cross, in a controlled environment in 2006 in the Agricultural Research Organization, The Volcani Center.

Asexual propagation of the new *Citrus deliciosa* Ten. variety 'SIGAL' by grafting onto 'Troyer' citrange—*Citrus sinensis* (L.) Osb. x *Poncirus trifoliata* L. (unpatented) was first performed in April 1996 in Bet Dagan, Coastal Plain, Israel, and has demonstrated that the combination of characteristics as herein disclosed for the new variety are firmly fixed and retained through successive generations of asexual propagation. The new variety propagates true-to-type.

BRIEF DESCRIPTION OF THE INVENTION

The following traits have been repeatedly observed and are determined to be characteristics of 'SIGAL', which in combination, distinguish this mandarin plant as a new, unique and distinct variety:

1. Easy-peeling;
2. Late-ripening;
3. High quality;
4. Excellent flavor;
5. Fruit shape at stalk end flattened;
6. Medium size fruit;

7. Dark orange skin color; and
8. Seedless fruit.

In comparison to the parental varieties, 'ORAH' (unpatented) and 'SHAM' (patented U.S. Plant Pat. No. 13,634), 'SIGAL' differs primarily in the traits listed in Table 1.

TABLE 1

Comparison of 'SIGAL' with its parent varieties.

| Characteristic | New variety 'SIGAL' | Female parent 'ORAH' (unpatented) | Male parent 'SHANI' (patented U.S. Plant Pat. No. 13,634) |
|---|---|---|---|
| Surface | medium rough | rather smooth | smooth |
| Fruit color of albedo | pale orange | white | reddish |
| Fruit filling of core | hollow | half filled | hollow |
| Color of rind | dark orange | orange | red orange |

Of the many commercial varieties known to the present inventors, the most similar in comparison to the new *Citrus deliciosa* Ten. 'SIGAL' is *Citrus deliciosa* Ten. 'MURCOTT' (unpatented), in the following characteristics described in Table 2.

TABLE 2

Comparison of 'SIGAL' with commercial variety.

| Characteristic | New Variety 'SIGAL' | Comparison Variety 'MURCOTT' (unpatented) |
|---|---|---|
| Surface | medium rough | rough |
| Fruit color of albedo | pale orange | pinkish |
| Fruit filling of core | hollow | filled |

BRIEF DESCRIPTION OF THE PHOTOGRAPHS

The accompanying photographs illustrate the overall appearance of the new *Citrus deliciosa* Ten. variety 'SIGAL' showing the colors as true as is reasonably possible with colored reproductions of this type. Colors in the photographs may differ slightly from the color values cited in the detailed morphological description, which accurately describe the color of 'SIGAL'. The depicted plant and plant parts of the new *Citrus deliciosa* Ten. Variety 'SIGAL' are of a thirteen year-old tree.

DETAILED MORPHOLOGICAL DESCRIPTION

Figure 1:
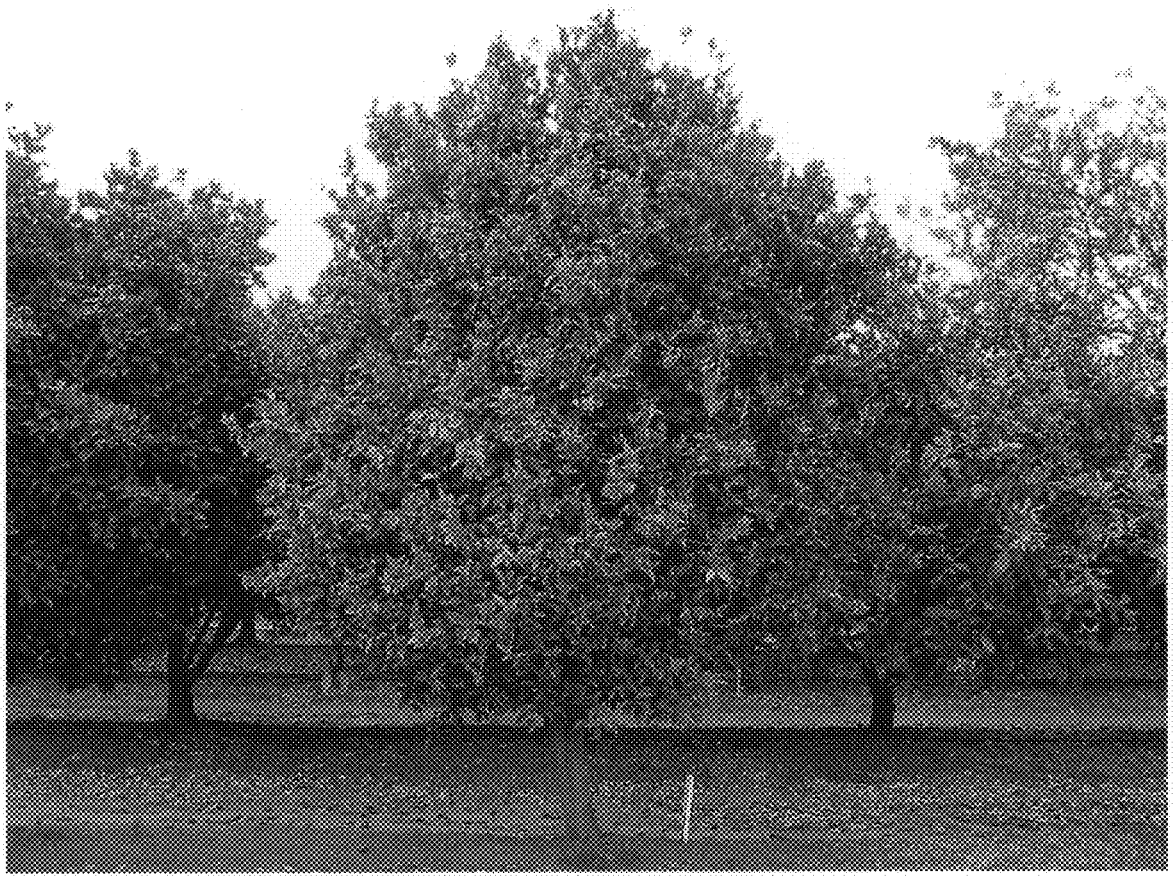
FIG. 1 shows an adult tree of 'SIGAL'.
Figure 2:
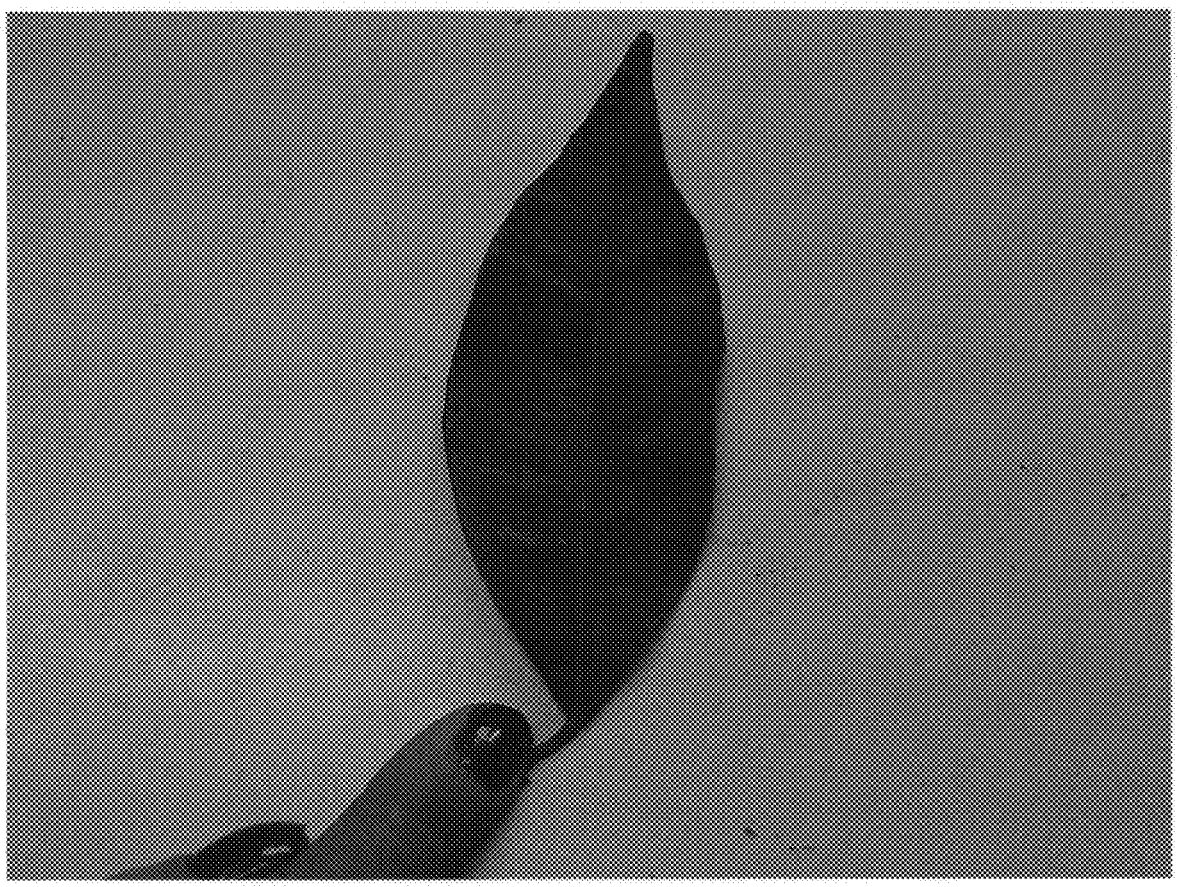
FIG. 2 shows a typical leaf of 'SIGAL'.
Figure 3:
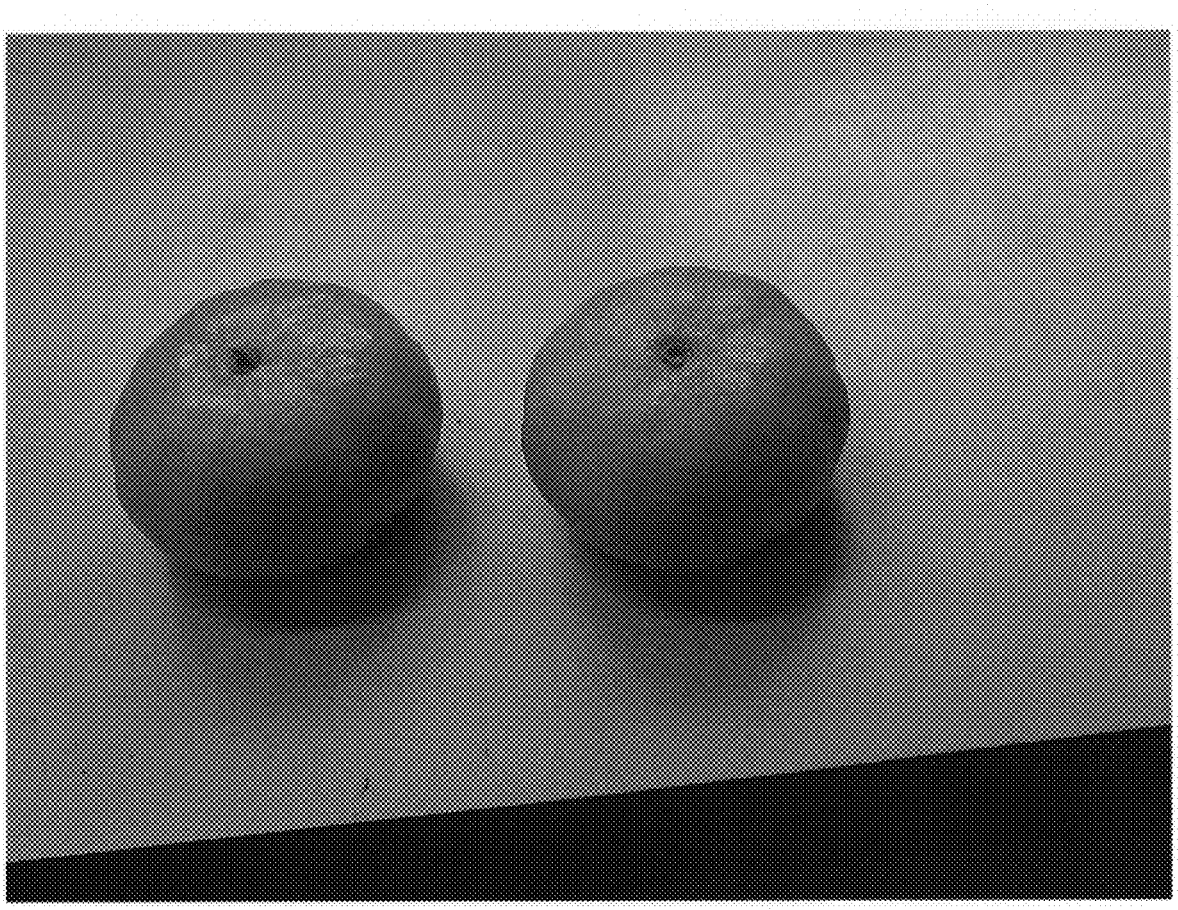
FIG. 3 shows a typical mature fruit of 'SIGAL', viewed at base and apex.
Figure 4:
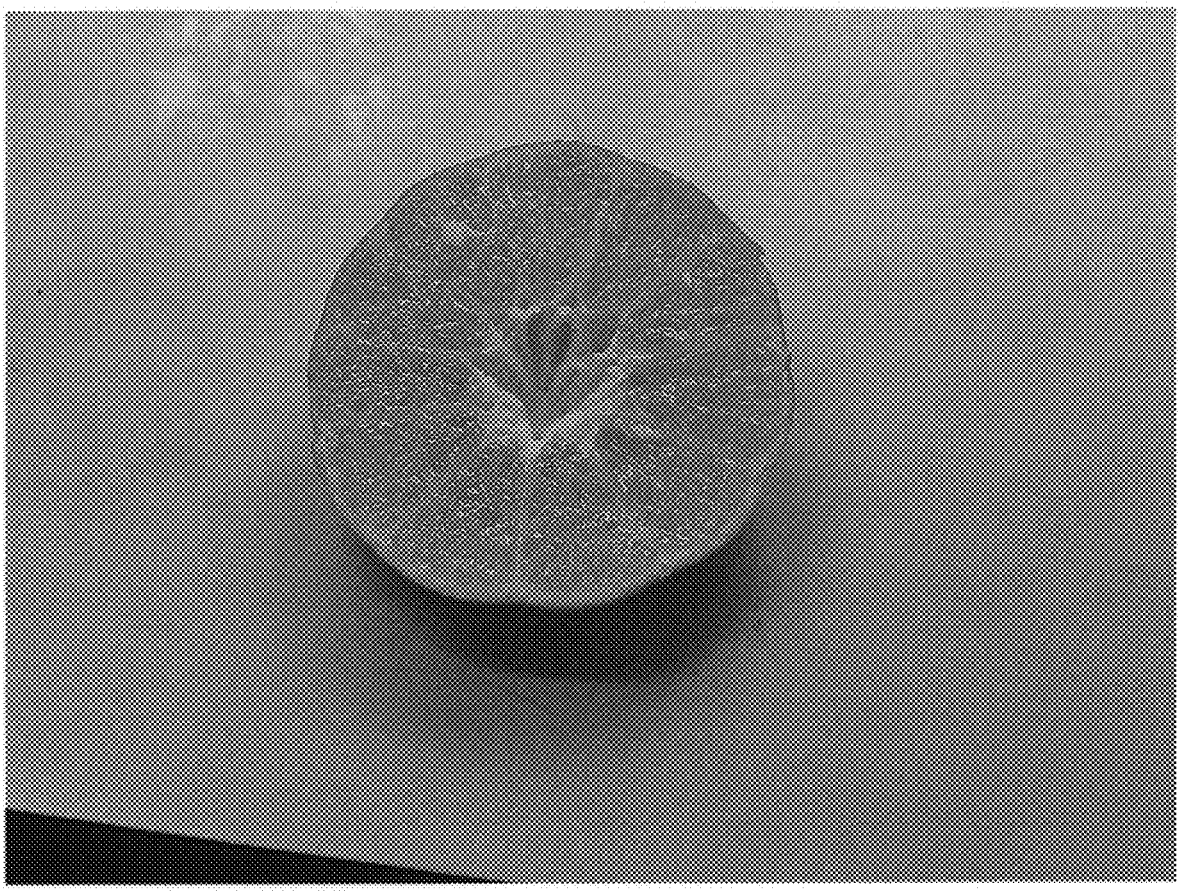
FIG. 4 shows a mature fruit of 'SIGAL' in cross section.
Figure 5:
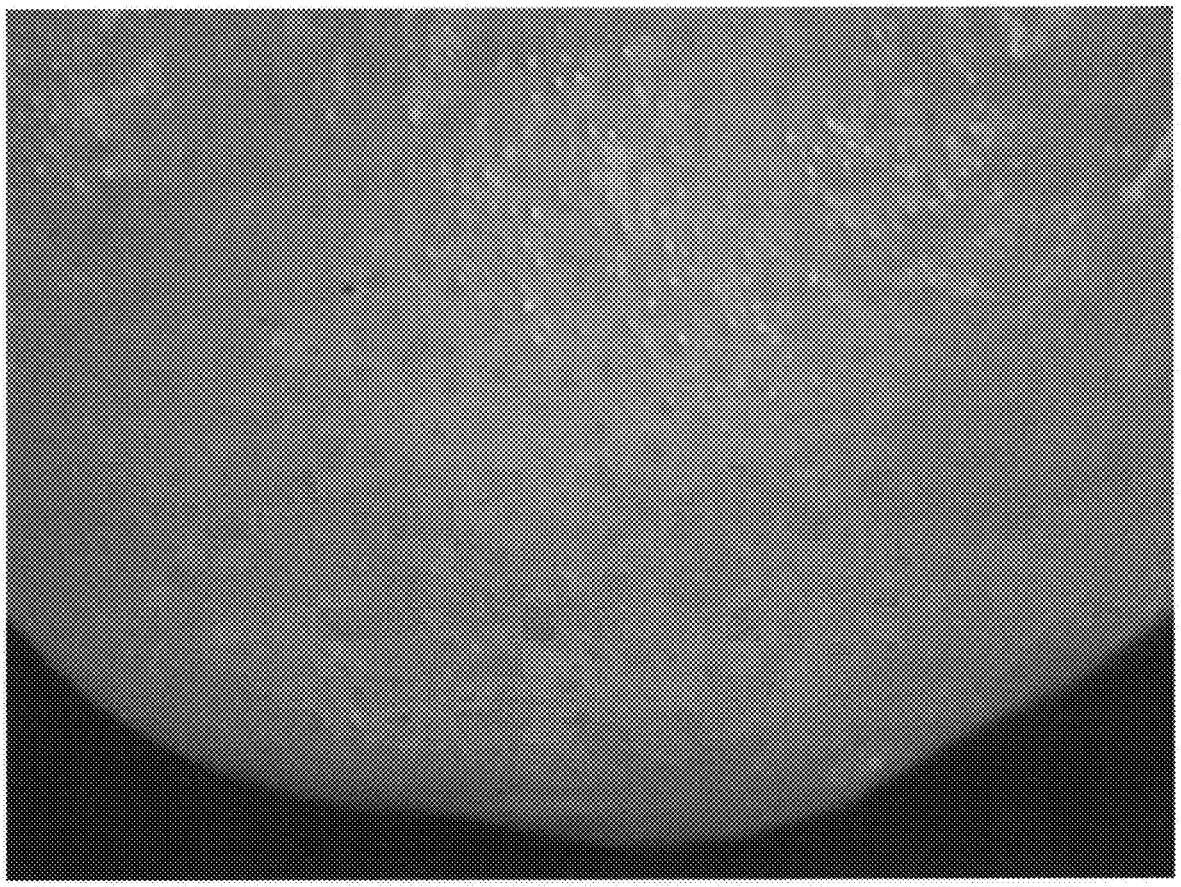
FIG. 5 shows a close-up view of skin oil glands of a mature fruit of 'SIGAL'.
Figure 6:
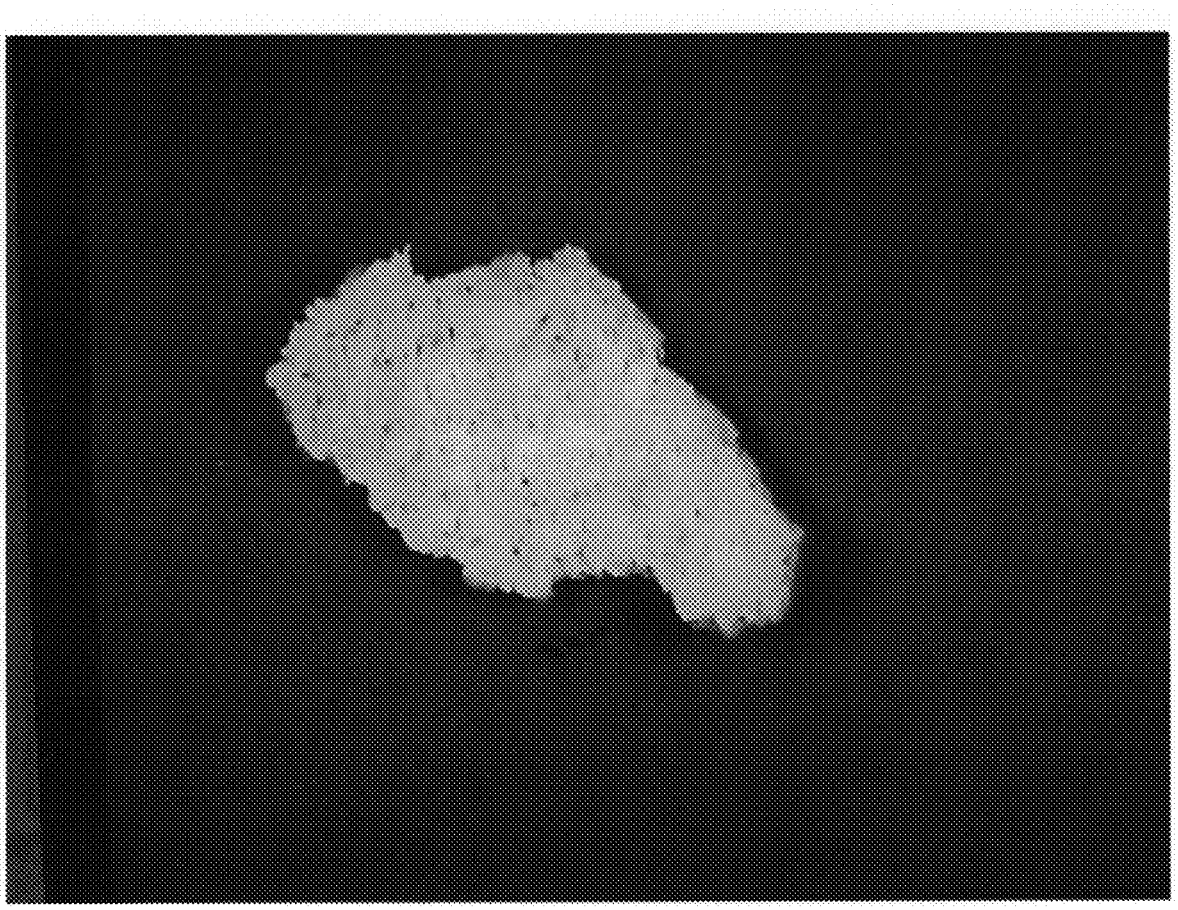
FIG. 6 shows the albedo on the inside peel of a mature fruit of 'SIGAL'.

The new *Citrus deliciosa* Ten. 'SIGAL' has not been observed under all possible environmental conditions. The phenotype of the new variety may vary with variations in environment such as temperature, light intensity, day length, soil or pruning, without any change in the genotype of the mandarin plant.

The aforementioned photographs, together with the following observations, measurements and values describe plants of 'SIGAL' as grown in the orchard in Bet Dagan, Coastal Plain, Israel, under conditions which closely approximate those generally used in commercial practice.

The described trees were grafted on 'Troyer' citrange—*Citrus sinensis* (L.) Osb. x *Poncirus trifoliata* L. (unpatented) and planted at a distance of 1.5×5 m in sandy red loam soil at an elevation of about 30 meters above sea level with irrigation of 100 $m^3$ per hectare during summer, and addition of 1 liter of fertilizers N:P:K;(7:3:7+micro-elements (trace elements)) per 1 $m^3$ of water. Average annual rainfall is about 550 mm, with an average of 350 mm of rainfall in winter (December to February). Mean diurnal minimum temperature in January is 7.2° C., and mean diurnal maximum temperature in July is 30.8° C.

Unless otherwise stated, the detailed morphological description includes observations, measurements and values taken from 2009 to 2011 and based on thirteen-year-old 'SIGAL' trees, grafted in 1996 and grown in the orchard in Bet Dagan, Coastal Plain, Israel. Quantified measurements are expressed as an average or a range of measurements taken from a number of plants of 'SIGAL'. The measurements of any individual plant, or any group of plants, of the new variety may vary from the stated average or range.

Color references are made to The Royal Horticultural Society Colour Chart (R.H.S.), (1986 edition), except where general colors of ordinary significance are used. Color values were taken under daylight conditions in full sunlight in Bet Dagan, Israel.

All of the plants of 'SIGAL', insofar as they have been observed, have been consistent in all the characteristics described below.

Classification:

*Botanical.*—*Citrus deliciosa* Ten.

Parentage:

*Female or seed parent.*—*Citrus deliciosa* Ten. 'ORAH' (unpatented).

*Male or pollen parent.*—*Citrus deliciosa* Ten. 'SHAM' (patented U.S. Plant Pat. No. 13,634).

Propagation: Grafting onto 'Troyer' citrange—*Citrus sinensis* (L.) Osb. x *Poncirus trifoliata* L. (unpatented).

Growing conditions:

*Light intensities.*—Full sunlight.

TABLE 3

Climatic growing conditions - temperatures and precipitation or rainfall

| | Jan. | Feb. | March | Apr. | May | Jun. | July | Aug. | Sep. | Oct. | Nov. | Dec. |
|---|---|---|---|---|---|---|---|---|---|---|---|---|
| Mean maximum air temperature (° C.) | 17.8 | 18.1 | 20.1 | 24.5 | 27 | 29.2 | 30.8 | 31.2 | 30.4 | 28.3 | 24.1 | 19.7 |

TABLE 3-continued

| Climatic growing conditions - temperatures and precipitation or rainfall | | | | | | | | | | | | |
|---|---|---|---|---|---|---|---|---|---|---|---|---|
| | Jan. | Feb. | March | Apr. | May | Jun. | July | Aug. | Sep. | Oct. | Nov. | Dec. |
| Mean minimum air temperature (° C.) | 7.2 | 7.1 | 8.8 | 11.5 | 14.6 | 17.9 | 20.6 | 21.2 | 19.4 | 16 | 11.8 | 8.6 |
| Mean rainfall (mm) | 140.5 | 96.9 | 66.1 | 17.5 | 2.2 | — | — | — | 0.4 | 20.4 | 76.2 | 130.3 |

*Fertilization*.—A balanced fertilizer with level of 7:3:7 (N:P:K)+micro-elements.

*Growth regulators*.—None applied.

*Pruning*.—Manual pruning is applied. The size and overall shape of mandarin trees essentially depend on pruning and spacing. 'SIGAL' was pruned creating a tree which is ovoid in shape with 2 or 3 main brunches. When the trees are freely grown, the size and the shape assumed by the trees are typical of *Citrus deliciosa* Ten.

TABLE OF CHARACTERISTICS

Tree:

*Age*.—Observed trees were thirteen years old.

*Fruit*.—Type: mandarin.

*Tree*.—Vigor: strong. Height: about 4 m. Diameter of crown: about 4 m. Overall shape: ovoid. Density of canopy: medium. No of main brunches: 2. Diameter of trunk: about 10 cm. Color of bark: dark gray closest to RHS 199 A. Surface of bark: slightly rough. Lenticels: not visible.

*Main branches*.—Attitude: nearly upright. Angle relative to trunk: about 15°. Length: about 3 m. Thickness: 10-15 cm. Typical and observed main branch internode length: internodes are not separately visible. Color of bark: dark gray closest to RHS 199 A. Surface of bark: rough. Lenticels: not visible.

*Water shoot*.—Water shoots were removed.

*Young leaf*.—Anthocyanin coloration: absent. Upper side green medium green RHS 137 C. Lower side medium green RHS 144 A. Surface: smooth. Glossiness: weak. Pubescence: very weak.

*Fully developed leaf blade*.—Length: 105-120 mm. Width: 44-55 mm. Shape in cross section: concave. Twisting: absent. Blistering: weak. Upper side dark green RHS 137 A. Lower side medium green RHS 144 A. Leaf shape: elliptic. Texture (upper surface): smooth. Texture (lower surface): smooth. Pubescence on upper side: absent. Pubescence on lower side: absent. Firmness: medium. Undulation of margin: absent. Depth of incisions of margin: very shallow. Shape of apex: acute. Shape of base: obtuse. Glossiness: medium. Venation pattern: reticulate. Upper side dark green RHS 137 A. Lower side medium green RHS 144 A.

*Petiole*.—Length: 14-18 cm. Thickness: about 1 mm. Width of wing: 1-2 mm. Width of wing relative to leaf blade: very narrow. Shape in cross section: straight. Upper side dark green RHS 137 A. Lower side medium green RHS 144 A. Pubescence: absent. Surface: smooth.

*Petiole wing*.—Color of upper side: dark green RHS 137 A. Color of lower side: medium green RHS 144 A. Surface: smooth.

*Flower bud*.—Anthocyanin coloration: absent. Shape: spherical. Color: greenish white RHS 157 A. Length: 5-8 mm. Diameter: 4-5 mm.

*Vegetative bud*.—Anthocyanin coloration: absent. Shape: spherical. Color: medium green RHS 144 A. Length: 2-3 mm. Diameter: 1-2 mm.

*Flower*.—No. of petals: 5. No. of flowers per axil node: one or few. Shape: star-like. Depth: about 7 mm. Diameter of corolla: 18-22 mm. Scent: typical for *Citrus*. Flowering period: starts end of March, duration about three weeks.

*Pedicel*.—Length: 4-5 mm. Shape in cross section: circular. Color: light green RHS 144 C. Thickness: about 1 mm.

*Sepal*.—Number: five. Shape: triangular with acute apex. Length: minuscule. Width: minuscule. Margin: entire.

*Calyx*.—Diameter: 5-6 mm. Color: between light yellowish green RHS 145 B and light green RHS 145 C. Shape: flattened. Shape of apex of lobe: acute. Size: miniscule.

*Petal*.—Shape: elongated. Length: 9-12 mm. Width: 4-7 mm. Color of upper side: white RHS 155 B. Color of lower side: white RHS 155 B. Texture of upper side: smooth. Texture of lower side: smooth. Apex: rounded with slight mucron. Margin: entire. Base: truncate.

*Stamina*.—Number: about 18.

*Anther*.—Length: less then 1 mm. Color: yellowish orange RHS 13 A. Shape: elongated.

*Filament*.—Length: 6-9 mm. Thickness: less than 1 mm. Color: white RHS 155 B.

*Pollen*.—Color: between very dark yellow RHS 13A and dark to very dark yellow RHS 13 B. Viability: low.

*Ovary*.—Shape: flattened-globose. Length: about 5 mm. Diameter: about 3 mm. Color: medium green RHS 137 C.

*Style*.—Length: 6-8 mm. Diameter: about 2 mm. Color: very light green RHS 144 D.

*Stigma*.—Shape: flattened rounded. Color: dark yellow RHS 13 C.

*Fruit*.—Fruit overall shape: flattened-rounded. Length: 45-54 mm. Diameter: 65-80 mm. Ratio length/diameter: shorter than broad. Position of maximum diameter: in the middle. Shape in cross section: rounded scalloped. Shape at stalk end: flattened. Depression at stalk end: absent. Neck: absent. Radial grooves at stalk end: absent. Floral disc below calyx: miniscule. Abscission layer between calyx and fruit: present.

Shape at distal end: flattened. Depression at distal end: present. Depth of depression at distal end: 1-2 mm. Diameter of depression relative to fruit: small. Areola: present. Conspicuousness of areola: very weak. Type of areola: smooth. Presence of areola: complete. Diameter of areola relative to fruit: large. Stylar scar: typical. Diameter of stylar scar: miniscule. Persistence of style: absent. Navel opening: sometimes present. Diameter of navel opening: medium. Protrusion of navel: absent. Radial grooves at distal end: absent. Main color of surface: dark orange RHS 28 B. Pubescence of surface: absent. Glossiness: medium. Roughness of surface: medium rough. Evenness of size of oil glands: even. Size of larger oil glands: about 1 mm. Conspicuousness of larger oil glands: weak. Pebbles on oil glands: dense. Color of oil glands: dark to very dark orange RHS 28 B. Firmness: firm. Thickness of rind: about 2 mm. Adherence of rind to flesh: weak. Strength of rind: weak. Oiliness of rind: weak. Oil glands on inner side: non conspicuous. Color of albedo: light orange RHS 27 C. Density of albedo: medium. Adherence of albedo to flesh: strong. Amount of fibers in albedo: few. Differently colored spots in flesh: none. Bicolored segments: none. Color of flesh: dark to very dark orange RHS 25 B. Texture of flesh: fine. Filling of core: hollow. Diameter of core: 17-21 mm. Number of non-developed segments: none or very few. Number of developed segments: many 11 or 12. Number of open segments: none. Adherence of segments: strong. Strength of segment wall: strong. Length of juice vesicle: 3-6 mm. Thickness of juice vesicle: 2-3 mm. Conspicuousness of vesicle wall: strong. Adherence of juice vesicles: strong. Presence of navel viewed internally: absent. Amount of fruit per tree per season: the amount of fruit per season is as a complex performance characteristic dependent on the age of the tree, climatic conditions and management like pruning, irrigation, and fertilization. Average Juice content: 46%. Average fruit weight: 130-155 g. Juice content: medium. Total soluble solids: 15.8. Acidity of juice: 1.2. Strength of fiber: medium. Number of seeds: none or very few undeveloped. Flowering habit: once per year. Fruit ripening: mid-January to mid-March. Parthenocarpy: present. Time of flowering March.

Disease resistance: Brown Spot, *Alternaria alternata* pv. *citri* pathotype tangarin Solel.

Pest resistance: No atypical resistance has been noted.

Disease susceptibility: None observed.

Pest susceptibility: None observed.

Shipping/storage characteristics: 'SIGAL' mandarins can be stored for a period of 3 to 6 weeks at low temperatures of between 2-8° C. 'SIGAL' mandarins are chilling tolerant, and are resistant to common cold quarantine insect disinfestation treatments.

We claim:

1. A new and distinct variety of mandarin, *Citrus deliciosa* Ten., tree named 'SIGAL', as illustrated and described herein.

* * * * *